United States Patent
Tomas (10) Patent No.: US 8,893,636 B2
(45) Date of Patent: Nov. 25, 2014

(54) APPARATUS FOR GRIPPING A CHAIN

(75) Inventor: Julek Romuald Tomas, Aberdeen (GB)

(73) Assignee: Subsea 7 Limited, Sutton (GB)

( * ) Notice: Subject to any disclaimer, the term of this patent is extended or adjusted under 35 U.S.C. 154(b) by 63 days.

(21) Appl. No.: 13/824,887

(22) PCT Filed: Sep. 19, 2011

(86) PCT No.: PCT/GB2011/051758
§ 371 (c)(1),
(2), (4) Date: Aug. 7, 2013

(87) PCT Pub. No.: WO2012/038730
PCT Pub. Date: Mar. 29, 2012

(65) Prior Publication Data
US 2013/0312649 A1    Nov. 28, 2013

(30) Foreign Application Priority Data

Sep. 20, 2010  (GB) .................................. 1015717.0

(51) Int. Cl.
*B63B 21/18*   (2006.01)
*G01N 3/08*    (2006.01)

(52) U.S. Cl.
CPC . *B63B 21/18* (2013.01); *G01N 3/08* (2013.01)
USPC ....................................................... 114/200

(58) Field of Classification Search
CPC .................................. B63B 21/18; G01N 3/08
USPC ......... 114/199, 200, 210; 24/116 R; 254/264; 715/234
See application file for complete search history.

(56) References Cited

U.S. PATENT DOCUMENTS

| | | | | |
|---|---|---|---|---|
| 3,289,626 A * | 12/1966 | Petrie et al. | ............ | 114/200 |
| 3,540,396 A | 11/1970 | Horton | | |
| 3,547,066 A * | 12/1970 | Bugaenko et al. | ............ | 114/200 |
| 3,638,599 A * | 2/1972 | Nilsen | ............ | 114/200 |
| 3,805,728 A * | 4/1974 | Abraham | ............ | 114/200 |
| 3,859,949 A * | 1/1975 | Toussaint et al. | ............ | 114/243 |
| 4,077,348 A * | 3/1978 | Broehl | ............ | 114/200 |
| 4,186,464 A * | 2/1980 | Sandoy | ............ | 24/116 R |
| 5,934,216 A | 8/1999 | Childers et al. | | |
| 6,431,102 B1 * | 8/2002 | Askestad et al. | ............ | 114/200 |
| 6,655,661 B2 * | 12/2003 | Hovik et al. | ............ | 254/264 |
| 7,240,633 B2 * | 7/2007 | Barlow | ............ | 114/200 |
| 7,284,196 B2 * | 10/2007 | Skeen et al. | ............ | 715/234 |
| 8,069,805 B2 * | 12/2011 | De Baan et al. | ............ | 114/230.26 |

FOREIGN PATENT DOCUMENTS

| | | |
|---|---|---|
| EP | 0 217 761 | 4/1987 |
| GB | 1114538 | 5/1968 |
| GB | 1141699 | 1/1969 |
| GB | 1 457 711 | 12/1976 |

* cited by examiner

*Primary Examiner* — Daniel V Venne
(74) *Attorney, Agent, or Firm* — Levy & Grandinetti (57) ABSTRACT

An apparatus for gripping a chain including a body which allows passage of the chain is disclosed. The body has first and second chain gripping devices, both adapted to grip the chain to restrict or prevent movement of the chain relative to the body. These first and second gripping devices are arranged in the body in respective first and second angular orientations which are offset with respect to one another, whereby the first and second chain gripping devices are adapted to grip respective links of the chain having different angular orientations. An associated method is also described.

28 Claims, 6 Drawing Sheets

APPARATUS FOR GRIPPING A CHAIN

This Application is the U.S. National Phase of International Application Number PCT/GB2011/051758 filed on Sep. 19, 2011, which claims priority to Great Britain Application No. 1015717.0 filed on Sep. 20, 2010.

The present invention relates to an apparatus for gripping a chain, particularly but not exclusively a chain used to anchor an object to an anchoring point, which can typically be a submerged anchoring point. The object being anchored can typically be buoyant and can be floating on the surface of the water (e.g. the sea) or can be submerged. In typical embodiments the object can be a buoy (e.g. a subsea production buoy) submerged at depth beneath the surface of the sea. The chain may be a mooring line and may be used to attach a subsea production buoy to the seabed. Such buoys are often used in deep water hydrocarbon production facilities. The invention also provides a method for gripping a chain, particularly but not exclusively, a chain used as above, e.g. to secure a subsea production buoy to an anchoring point, typically using a plurality of chains connecting the object to a corresponding number of spaced apart anchoring points e.g. on the sea bed.

According to the first aspect of the present invention, there is provided an apparatus for gripping a chain, the apparatus comprising a body allowing passage of the chain relative to the body;
the body having a first chain gripping device, adapted to grip the chain to restrict or prevent movement of the chain relative to the body; and
a second chain gripping device, adapted to grip the chain to restrict or prevent movement of the chain relative to the body;
the first and second gripping devices being arranged in the body in respective first and second angular orientations which are offset with respect to one another, whereby the first and second securing devices are adapted to grip respective links of the chain having different angular orientations.

The invention also provides a method of gripping a chain, the method comprising providing a body allowing passage of the chain relative to the body;
the body having a first chain gripping device, adapted to grip the chain to restrict or prevent movement of the chain relative to the body; and a second chain gripping device, adapted to grip the chain to restrict or prevent movement of the chain relative to the body; the first and second gripping devices being arranged in the body in respective first and second angular orientations which are offset with respect to one another, whereby the first and second securing devices are adapted to grip respective links of the chain having different angular orientations;
wherein the method comprises gripping a first link of the chain with the first gripping device, the first link of the chain being in a first angular orientation and aligned with the first gripping device; and,
gripping a second link of the chain with the second gripping device, the second link of the chain being in a second angular orientation and aligned with the second gripping device.

Each chain gripping device may comprise a pair of dogs or other gripping mechanisms, although in more simple embodiments, a single dog can suffice for each gripping device. Where a pair of dogs is provided in each gripping device, the pair of dogs in each device can optionally be aligned with one another on opposite sides of the chain, e.g. typically along a common line passing through the axis of the chain. For example, in the first securing device, the angular orientation of the pair of dogs can be 0 degrees and at 180 degrees with respect to the axis of the body (which is typically aligned with the long axis of the chain), so that the dogs of the first gripping device are aligned with one another at opposite sides of the chain, and can move in a straight line towards and away from the chain to grip the chain between the two dogs. The angular orientation of the second gripping device can be 90 degrees and at 270 degrees, so that the dogs of the first gripping device are also aligned with one another at opposite sides of the chain, and can move in a straight line towards and away from the chain to grip the chain between the two dogs, but the angular orientation of the first gripping device is not the same as the second, i.e. the two devices are perpendicular to one another. This is particularly suitable for chains with adjacent links that are perpendicular to one another with the same offset angular orientation of immediately adjacent links. The offset of the adjacent links of the chain is used to determine the offset between the two gripping devices, so that the gripping devices are aligned with the links of the chain being used. In some embodiments, to be used with different designs of chain where the adjacent links in the chain are offset by some other angle, e.g. less than 90 degrees, then the matching angle (e.g. 65 degrees etc) can be used in the offset of the gripping devices so that the first and second gripping devices can grip respective links of the chain even if these are not perpendicular.

In typical embodiments of the invention, the first and second gripping devices are located in the same axial plane of the body. In some other embodiments, the gripping devices could be axially spaced apart in different axial planes in the body to engage with spaced apart links of the chain.

In typical embodiments of the invention the first and second gripping devices do not engage the chain at the same time. For example, when the first gripping device is engaged with the chain and is resisting axial movement of the chain and the body, typically the second gripping device is disengaged from the chain and is not resisting axial movement of the chain and the body. Thus the first and second gripping devices typically grip the chain at different times.

Typically the different links of the chain being gripped by the respective gripping devices are adjacent links, but this is not necessary and embodiments of the invention are possible where the first and second gripping devices engage with respective links that are axially spaced apart on the chain and are not adjacent.

The gripping devices can be engaged and disengaged from the chain by axial movement of the chain through or past the body. The gripping devices can optionally engage and grip the chain to restrict or prevent movement of the chain in one axial direction through or past the body, but may typically allow movement of the chain in the opposite axial direction through or past the body. This allows tensioning of the chain by pulling it through or past the body so that the gripping devices allow passage of the chain in the first direction to apply tension to the chain, and restrict or prevent loosening of the chain by movement of the chain through or past the body in the opposite direction. The gripping devices thereby typically function as a ratchet mechanism.

The offsetting of the first and second gripping devices to engage different links of the chain means that once a single link has moved past the first gripping device in the first direction (e.g. when being tensioned) it cannot pass back through the first gripping device in the opposite direction to relieve tension on the chain, because the chain is then being held in that position by the second gripping device which engages a different link of the chain. Therefore, embodiments of the invention allow fine tuning of the tension of the chain one link at a time and also the deployed length of the chain one link at a time.

The or each dog is typically pivotally connected to the body to rotate around eccentric pivot points on the dog, typically located at or near one end of each dog.

Typically the or each dog is located on a radius with respect to the axis of the chain, and the or each dog engages the chain at the radially inner end (or head) of the dog. The eccentric pivot point may be located closer to the radially outer end (or tail) of the dog.

The or each dog may be disengaged from the chain by operation of a control device, which interacts with the or each dog to disengage it from the chain and allow movement of the chain through or past the body in both axial directions. The control device can interact with the radially outer end (or tail) of the dog to cause the dog to pivot around the eccentric pivot point and so disengage the head of the dog from the chain, thereby removing or reducing the restriction on the movement of the chain through or past the body. Typically the control device disengages all of the dogs from the chain at the same time.

The control device can comprise a sleeve or collar, which can move axially on the body relative to the pivot points of the dogs, typically interacting with the tail of the or each dog, optionally at the same time.

Typically the or each tail protrudes beyond an circumferential surface of the collar or sleeve, so that the axial movement of the collar or sleeve presses the collar or sleeve against the tail of the dog and disengages the dogs from the chain.

The collar or sleeve can be resiliently biased out of engagement with the dogs.

The collar or sleeve can optionally be pressed into engagement with the dogs by compression of a resilient device biasing the collar or sleeve away from engagement with the dogs. The collar or sleeve may be formed at one axial end of the body, spaced away from the eccentric pivot points of the or each dog, and can optionally be moved in and out of engagement with the or each dog by a clamp device pressing the sleeve against the body.

Optionally the chain may form part of a tension leg structure such as a tension leg platform for oil or gas exploration or recovery.

Optionally the apparatus incorporates an alignment device to control radial alignment of the gripping devices with respect to the chain links. Typically the alignment control device comprises a guide device to feed the chain into the body in a defined orientation in which the links of the chain are aligned with the first and second gripping devices. The guide device can comprise an inlet mask in the form of an aperture having the same outline as the chain in plan view.

The apparatus may include a measuring device such as a strain gauge to measure and optionally transmit to a recorder the tension on the chain.

In some embodiments, the contact between the chain and components of the apparatus is reduced and therefore the possibility of wear of the chain and the rest of the apparatus is reduced.

In some embodiments of the invention, the apparatus is located between the anchor and the object, and is typically suspended from the object so that the chain passes through the gripping devices (and optionally through the body) before connecting to the object being anchored (e.g. the buoy).

Optionally the apparatus is connected to the object being anchored (e.g. the buoy) by a pivotable connection (optionally incorporating a swivel) allowing the line of the chain approaching the buoy to change by swivelling of the pivotable connection whereby torque and lateral forces are isolated from the buoy by the pivotable connection.

Certain embodiments of the invention allow more precise tensioning of anchoring chains securing a subsea production buoy to anchoring points on the sea bed. This allows more control over the pitch and tilt of the subsea production buoy while submerged, and facilitates load sharing between multiple tendons, especially if they are close together.

The various aspects of the present invention can be practiced alone or in combination with one or more of the other aspects, as will be appreciated by those skilled in the relevant arts. The various aspects of the invention can optionally be provided in combination with one or more of the optional features of the other aspects of the invention. Also, optional features described in relation to one embodiment can typically be combined alone or together with other features in different embodiments of the invention.

Various embodiments and aspects of the invention will now be described in detail with reference to the accompanying figures. Still other aspects, features, and advantages of the present invention are readily apparent from the entire description thereof, including the figures, which illustrates a number of exemplary embodiments and aspects and implementations.

The invention is also capable of other and different embodiments and aspects, and its several details can be modified in various respects, all without departing from the spirit and scope of the present invention. Accordingly, the drawings and descriptions are to be regarded as illustrative in nature, and not as restrictive. Furthermore, the terminology and phraseology used herein is solely used for descriptive purposes and should not be construed as limiting in scope. Language such as "including," "comprising," "having," "containing," or "involving," and variations thereof, is intended to be broad and encompass the subject matter listed thereafter, equivalents, and additional subject matter not recited, and is not intended to exclude other additives, components, integers or steps. Likewise, the term "comprising" is considered synonymous with the terms "including" or "containing" for applicable legal purposes.

Any discussion of documents, acts, materials, devices, articles and the like is included in the specification solely for the purpose of providing a context for the present invention. It is not suggested or represented that any or all of these matters formed part of the prior art base or were common general knowledge in the field relevant to the present invention.

In this disclosure, whenever a composition, an element or a group of elements is preceded with the transitional phrase "comprising", it is understood that we also contemplate the same composition, element or group of elements with transitional phrases "consisting essentially of", "consisting", "selected from the group of consisting of", "including", or "is" preceding the recitation of the composition, element or group of elements and vice versa.

All numerical values in this disclosure are understood as being modified by "about". All singular forms of elements, or any other components described herein are understood to include plural forms thereof and vice versa.

In the accompanying drawings.

Referring now to the drawings, an anchor chain 1 is typically used to anchor an object such as a subsea oil and gas production buoy below a floating production storage and offloading unit (FPSO), although other applications of embodiments of the invention are contemplated. The chain 1 is connected to the buoy at a hanger porch H. A number of hanger porches are spaced apart on the buoy and each porch typically connects an anchor chain 1 to the seabed and holds it in tension against the positive buoyancy of the buoy. A tensioning device T above the hanger porch applies tension to the chain 1. The hanger porch H allows the chain 1 to pivot relative to the hanger porch H.

A chain gripping device 10 according to the invention is connected below the hanger porch H, typically held in tension between the porch and the sea bed anchor (not shown). Connecting the chain gripping device below the porch allows inspection of the chain between the porch and the chain gripping device 10. Typically the connection between the porch and the chain gripping device 10 is articulated, allowing relative movement of the chain gripping device 10 relative to the porch, which is useful to reduce bending and torsional moments on the chain.

Figures 4, 5:
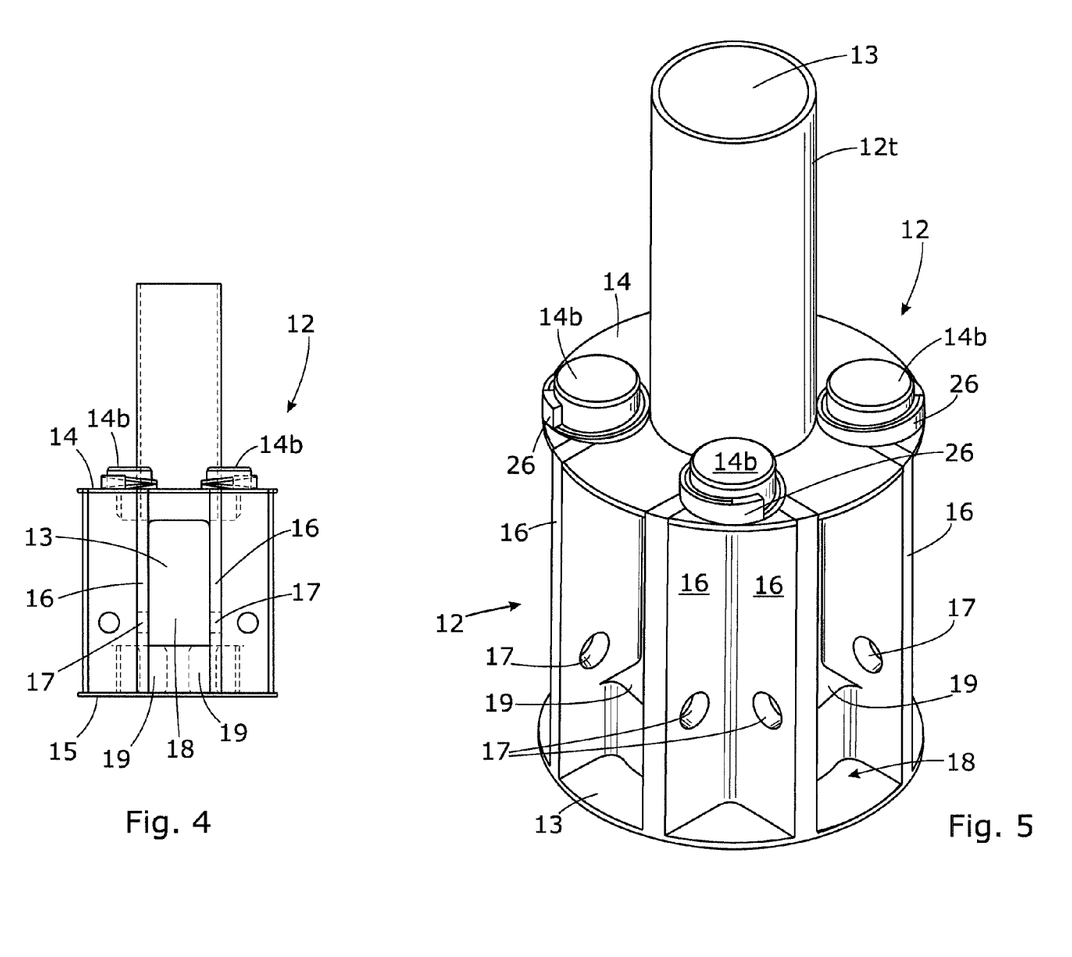
FIG. 4 is a side view of a body of the FIG. 1 apparatus.
FIG. 5 is a perspective view of the FIG. 4 body.
Figure 6:
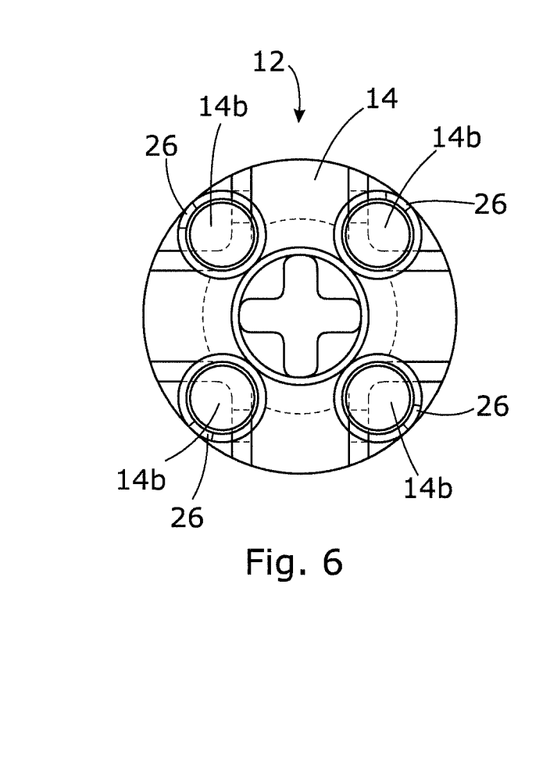
FIG. 6 is a plan view of the FIG. 4 body.

The chain gripping device 10 comprises a body 12 (FIGS. 4-6), first and second gripping devices 20 in the form of a first pair of dogs 20a and a second pair of dogs 20b, and a control sleeve 25. The body 12 is generally cylindrical in shape with an upper and lower end, and has a central bore 13 through which the chain 1 can pass between the two ends. The body 12 has a circular top plate 14 at the upper end and a circular bottom plate 15 at the lower end. The top plate 14 has a tubular extension 12t extending in axial alignment with the bore 13, to house the chain 1. The top plate 14 also has upwardly facing bosses 14b spaced equidistantly around the top plate 14.

Between the top and bottom plates 14, 15, a plurality of axial plates 16 extend in a web between the top and bottom plates, parallel to the inner bore 13. The plates 16 are provided in pairs that are parallel to one another. Each pair defines a housing 18 for a dog 20. Each plate 16 has an aperture 17 extending laterally through the plate 16. The apertures 17 are all located in the same plane, and receive pivot pins to define pivot axes for the dogs 20 to pivot within the housings 18.

Figure 7:
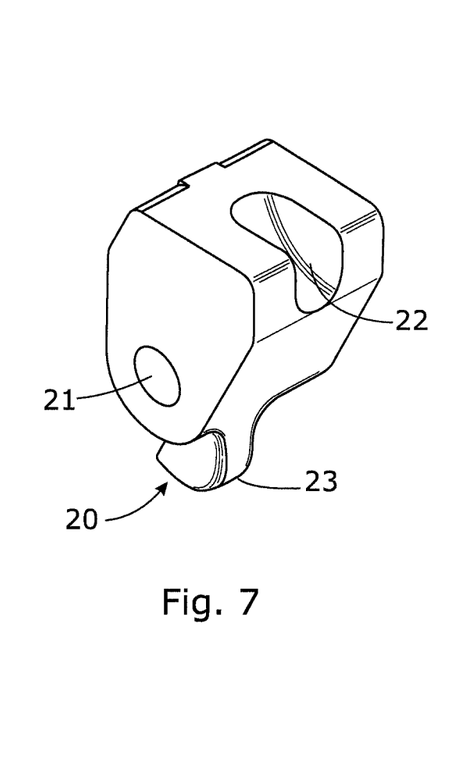
FIG. 7 is a perspective view of a dog of the FIG. 1 apparatus.
Figure 8:
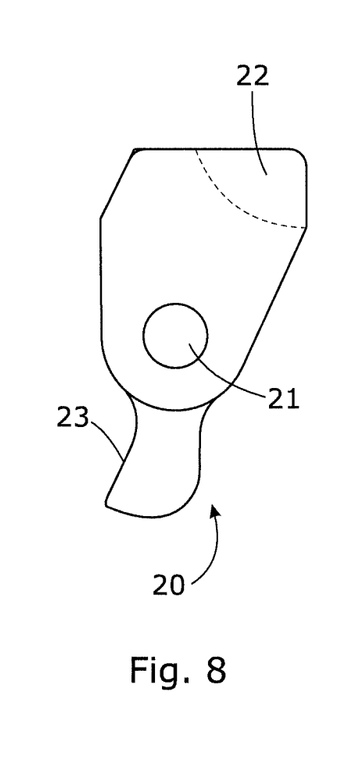
FIG. 8 is a side view of the FIG. 7 dog.
Figure 11:
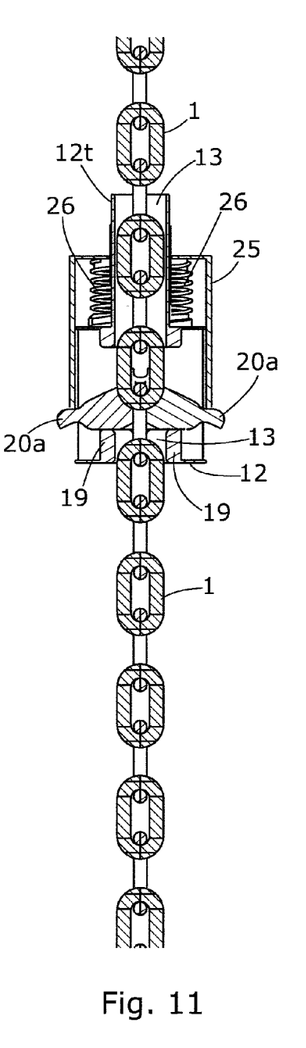
FIG. 11 is a section view through the line A-A of FIG. 10.
Figures 12, 13:
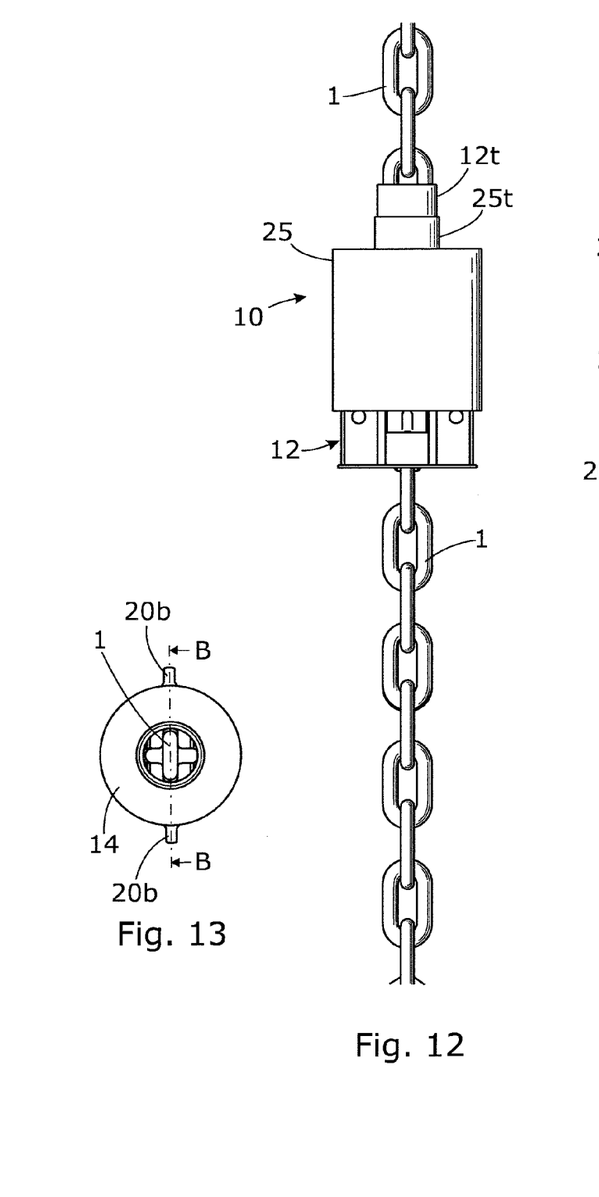
FIG. 12 is a side view of the apparatus in a second configuration.
FIG. 13 is a plan view of the FIG. 12 arrangement.

The dogs 20 (see FIGS. 7 and 8) are substantially identical, and have an eccentric aperture 21 placed between a head 22 and a tail 23, but typically closer to the tail 23 than to the head. The head 22 of each dog 20 has a recess to receive a link of the chain. The recess has side walls which restrain the link within the recess in a particular orientation. The two dogs 20 in each pair (e.g. dogs 20a) combine to substantially enclose the lower end of a single link of the chain 1 within the recesses of each head 22 when the dogs 20a are pivoted with their heads down into a first position in engagement with the chain 1 as best shown in FIG. 11. In the first position, the dogs 20 are generally horizontal as shown in FIG. 11, with their heads supported from below against further downward pivotal rotation by a stop member 19 extending upwards from the bottom plate 15. In this configuration, the tails 23 of the dogs 20 extend beyond the circumference of the top and bottom plates 14, 15, as best shown in FIG. 11.

Figure 14:
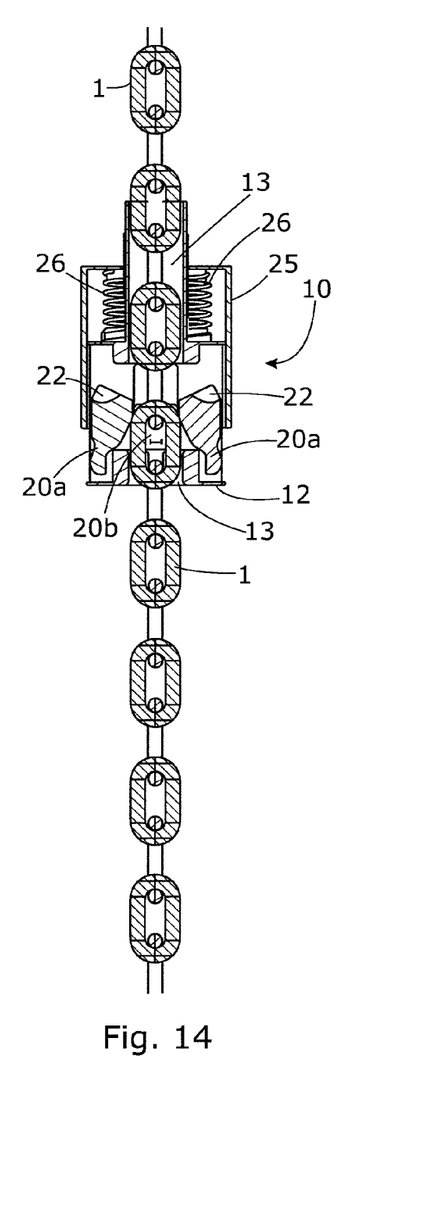
FIG. 14 is a section view through the line B-B of FIG. 13.
Figure 15:
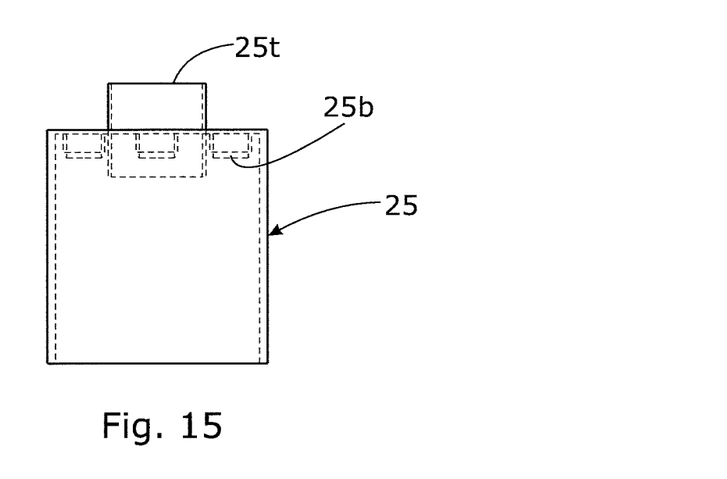
FIG. 15 is a side view of a control collar of the FIG. 1 apparatus.
Figure 16:
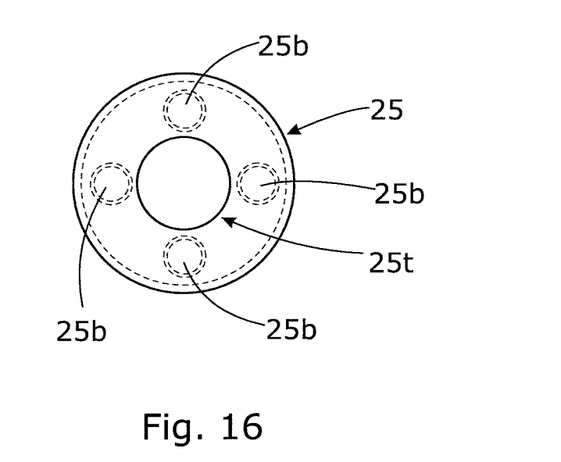
FIG. 16 is a plan view of the FIG. 15 control collar.

The dogs 20 can adopt a second position as best shown by the dogs 20a in FIG. 14. In the second position shown by the dogs 20a in FIG. 14, the dogs 20a have pivoted into a generally upright configuration, with their heads 22 disengaged from the chain 1 and their tails 23 disposed inside the circumference of the top and bottom plates 14, 15.

The control sleeve 25 is generally cylindrical, with a central bore and an upper end that is closed by an upper plate and having a tubular extension 25t extending from its upper end coaxially with the central bore of the sleeve 25. The lower end is open and is adapted to receive the body 12, over which it slides and can move axially, and in the assembled device 10, the tubular extension 25t slides over the tubular extension 12t. The cylindrical control sleeve slides over the radially outermost surfaces of the axial plates 16 in a close tolerance. The lower surface of the top plate of the control sleeve 25 has downwardly facing bosses 25b which are aligned with the upwardly extending bosses 14b of the body. Springs 26 are disposed between the bosses so that the control sleeve 25 is resiliently biased away from the upper plate 14 of the body 12. The springs 26 can typically be compressed to drive the control sleeve 25 over the body. This results in the lower end of the control sleeve 25 sliding over the tails 23 of the dogs 20 that are protruding beyond the outer circumference of the top and bottom plates, since the control sleeve 25 fits over the body 12 with a relatively close tolerance. Pressing down on the tails 23 rotates any dogs 20 into the second position in which they are generally upright as best shown by the dogs 20a in FIG. 14, thereby disengaging all of the dogs 20 from the chain 1.

Figures 9, 10:
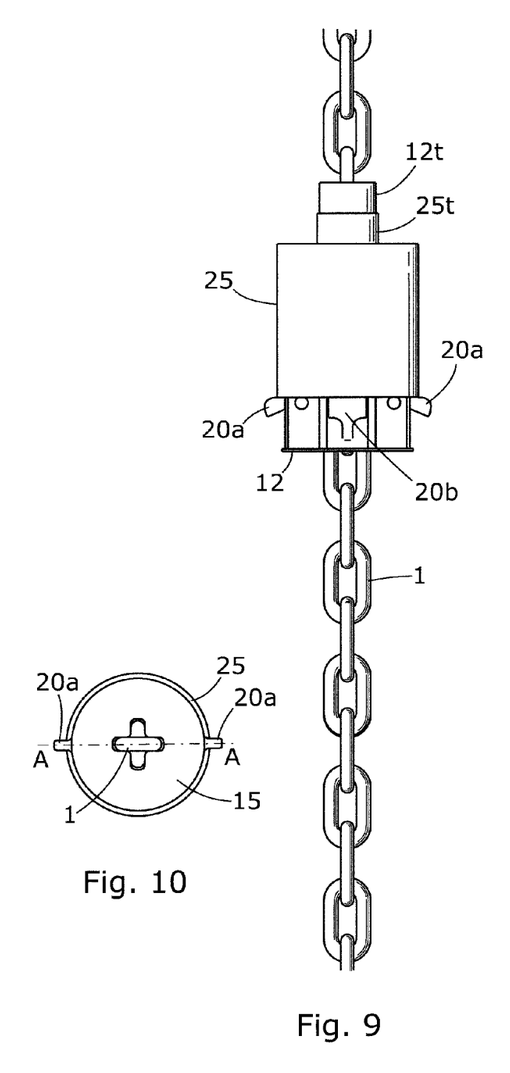
FIG. 9 is a side view of the apparatus in a first configuration.
FIG. 10 is a plan view of the FIG. 9 arrangement.

The bottom plate 15 has an inlet mask comprising a central aperture in the form of a cross (best seen in FIG. 10) to guide the chain 1 into the bore 13 in a particular orientation to line up the links of the chain 1 with the dogs 20. The chain 1 is typically under very high tension and rotation of the chain is usually difficult under load, so typically the device 10 can swivel around its connection to the hanger H to orientate itself with the chain 1.

Figure 1:
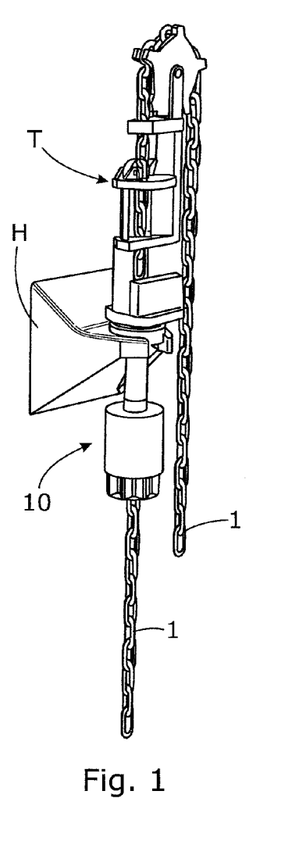
FIG. 1 is a perspective view of a first embodiment of apparatus for gripping a chain.
Figure 2:
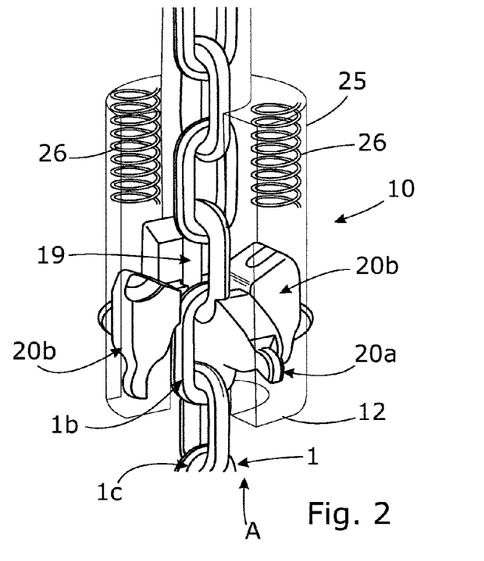
FIG. 2 is a close up view of the FIG. 1 apparatus in a first configuration.

Adjacent chain links are typically oriented perpendicularly to one another. As the chain 1 moves through the bore 13 of the body 12, the body is swivelled to align the two perpendicular pairs of dogs 20a, 20b with the perpendicular links of the chain. Referring now to FIG. 2, a particular chain link 1a will be aligned in the same plane as one of the two pairs of dogs 20. In the example shown in FIG. 2, the first link 1a is aligned in the same plane as the first pair of dogs 20a, which are configured in the first position, lying generally horizontal, with their heads 22 engaging the lower end of the link 1a. The link 1a is then free to move in the direction of the arrow A, upwardly through the bore 13 of the body 12, but is held against rotation by means of the recesses in the heads 22 that are engaged with the link 1a. Also, the link 1a is held against downward movement in the opposite direction to arrow A because the dogs 20a engaged with the link 1a underlie the link 1a, and are prevented from further downward rotation by the stop member 19 on the body 12. The link 1a is therefore free to move upwards in the bore 13, but cannot move downward and cannot rotate.

While link 1a is engaged with the dogs 20a, the dogs 20b which are perpendicular to dogs 20a are not in alignment with the plane of the link 1a, and pushed out of engagement with the chain by upper end of the next lowest link 1b, immediately underneath link 1a, as shown in FIG. 2. The second pair of dogs 20b are in alignment with the second link 1b, as this is perpendicular to first link 1a, but the second pair of dogs cannot grip the second link 1b at this point, as the recesses of the second pair of dogs 20b are pivoted out of engagement with the chain by the upper end of the second link 1b pressing on the lower surface of the second pair of dogs 20b, thereby moving them into the upright configuration, out of engagement with the chain. Therefore, only the first pair of dogs 20a engage with the chain 1 and restrict its movement through the device 10 when in the 2 first configuration as shown in FIG. 2.

Applying tension to the chain 1 by means of the tensioning device T above the hanger H pulls the chain 1 through the bore in the direction of the arrow A. Accordingly the first link 1a moves upwards out of engagement with the dogs 20a in the direction of the arrow A. The second pair of dogs 20b are still held in the upright configuration shown in FIG. 2 out of engagement with the second link 1b and the lower surfaces of the heads 22 of the second pair slide down the parallel sides of the second link 1b, which is in the same plane as the second pair of dogs 20b. In a similar manner, the next lowest (third) link 1c immediately below the second link 1b lifts up the heads 22 of the first pair of dogs 20a, which are in the same plane as the third link 1c, and begins to move them out of engagement with the chain 1, towards the upright position.

Figure 3:
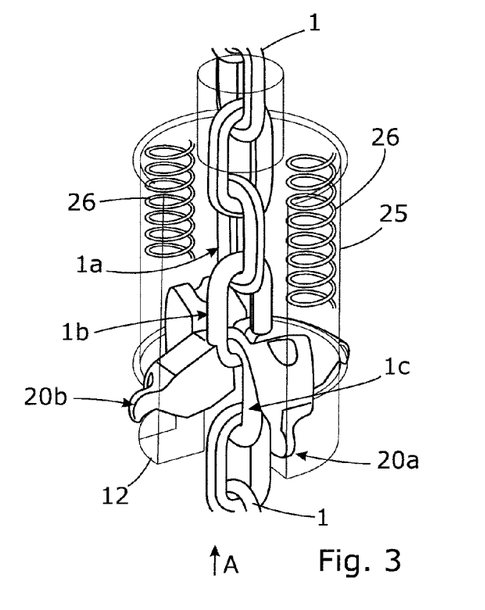
FIG. 3 is a close up view of the FIG. 1 apparatus in a second configuration.

The upward movement of the chain 1 continues in the direction of the arrow A until the parallel sides of the second link 1b move past the heads of the second dogs, and reach the position shown in FIG. 3, where the second dogs 20b pivot around their axes 17 into the horizontal position where they engage the lower end of the second link 1b in the recess in their heads 22, and restrict its rotational and downward movement. The first pair of dogs 20a are held in the upright position, out of engagement with the chain 1 by the upper ends and parallel sides of the third link 1c. The process continues in a similar manner with successive links below the link 1c.

Typically the chain alignment above the chain gripping device 10 is maintained by rotationally connecting the tensioning device T to the chain gripping device 10, e.g. by welding, so that the tensioning device T and the chain gripping device 10 are rigidly connected and move as a unit relative to the hanger porch H, thereby preventing or restricting torsional forces on the chain above the gripping device 10. Additional rotation prevention and restriction devices (such as the inlet mask in the lower plate 15) can be optionally provided above the chain gripping device in order to maintain the chain in the same orientation.

Thus the chain 1 has moved upwards through the device 10 by a distance of one link, and is held in the body against slackening in the start and stop positions of the chain.

When the chain gripping device is to be released, the dogs 20 can all be disengaged from the chain by operation of the control sleeve 25. The sleeve 25 is biased away from the body 12 by the springs 26. The lower end of the sleeve 25 is therefore spaced above the pivot points 17 in the body, and although it is a close fit on the body 12, the sleeve 25 does not interfere with the movement of the tails 23 of the dogs 20 beyond the outer circumference of the body because of this spacing. Thus, while the control sleeve 25 is spaced away from the body as shown in the figures, the dogs can operate normally, moving into and out of engagement with the chain as described above. When the chain tension is to be released the dogs are to be locked out of engagement by operation of the control sleeve 25. In this operation, the control sleeve is pushed towards the body, compressing the springs 26 between the two components. This can be done by an ROV (remotely operated vehicle) which can apply a clamp across the two components. Other methods of moving the control sleeve can be used instead or as well. When the control sleeve 25 moves towards the body 12, the lower end of the control sleeve 25 pushes the tails 23 of the dogs 20 downwards, causing any dogs 20 that are in the horizontal to pivot into the upright disengaged position and to release the chain.

Instead of (or as well as) using an ROV to operate the control sleeve, the tensioning device can optionally incorporate a push rod that presses on the control sleeve to compress the springs as described above.

Typically the tensioning device can be removed from the hanger porch after the chain has been tensioned to a suitable extent, which avoids the need to leave the tensioning device submerged for long periods. The tensioning device can optionally be re-connected at decommissioning.

The dogs 20 are all typically mounted eccentrically in the housings 18, so that the dogs 20 tend to adopt the horizontal engaged position shown by the first pair of dogs 20a in FIGS. 2 and 11, unless they are moved into the upright disengaged position (see the same first pair of dogs 20a in FIGS. 3 and 14) by movement of the chain 1 or by operation of the control sleeve 25.

Certain embodiments of the invention can allow enhanced control of tension in chains of submerged buoys, preventing or controlling the relative tension between chains anchoring the buoy and maintaining the orientation and lateral position of the moored buoy.

Embodiments of the invention allow gripping and tensioning and other handling of chain lines and other types of lines incorporating other materials such as wire or fibre rope, by connecting the wire or fibre rope or the like to chain terminals and running the chains through the chain gripping devices according to the invention, to grip them while being tensioned. Thus, anchor lines comprising lengths of wire rope connected to terminals with lengths of chain can be tensioned by applying the tension to the line and gripping the chain terminal section of the line only.

Modifications and improvements can be incorporated without departing from the scope of the invention.

The invention claimed is:

1. An apparatus for gripping a chain, the apparatus comprising a body having a body axis and allowing passage of the chain relative to the body along the body axis;
   the body having a first chain gripping device, adapted to grip the chain to restrict or prevent movement of the chain relative to the body; and
   a second chain gripping device, adapted to grip the chain to restrict or prevent movement of the chain relative to the body;
   the first and second chain gripping devices being arranged around the body axis in respective first and second angular orientations towards the body axis which are perpendicular to one another, whereby the first and second chain gripping devices are adapted to grip respective links of the chain that are perpendicular to one another.

2. An apparatus as claimed in claim 1, wherein each chain gripping device comprises a pair of dogs.

3. An apparatus as claimed in claim 2, wherein each dog in the pair of dogs in each gripping device is aligned with the other dog on opposite sides of the chain.

4. An apparatus as claimed in claim 1, wherein the first and second gripping devices are located in the same axial plane of the body.

5. An apparatus as claimed in claim 1, wherein the first and second gripping devices are axially spaced apart in different axial planes in the body to engage with spaced apart links of the chain.

6. An apparatus as claimed in claim 1, wherein the apparatus is adapted so that the first and second gripping devices do not engage the chain at the same time.

7. An apparatus as claimed in claim 1, wherein the first and second gripping devices are adapted to be engaged and disengaged from the chain by axial movement of the chain through or past the body.

8. An apparatus as claimed in claim 7, wherein the first and second gripping devices are adapted to engage and grip the chain to restrict or prevent movement of the chain in one axial direction through or past the body, but are adapted to allow movement of the chain in the opposite axial direction through or past the body.

9. An apparatus as claimed in claim 2, wherein each dog is pivotally connected to the body to rotate around eccentric pivot points on the dog.

10. An apparatus as claimed in claim 9, wherein each dog is located on a radius with respect to the axis of the chain, and each dog engages the chain at the radially inner end of the dog.

11. An apparatus as claimed in claim 10, wherein the eccentric pivot point is located closer to the radially outer end of the dog.

12. An apparatus as claimed in claim 9, wherein each dog may be disengaged from the chain by operation of a control device, which interacts with the dog to disengage it from the chain and allow movement of the chain through or past the body in both axial directions.

13. An apparatus as claimed in claim 12, wherein the control device disengages all of the dogs from the chain at the same time.

14. An apparatus as claimed in claim 13, wherein the control device comprises a sleeve or collar adapted to move axially on the body to interact with each dog.

15. An apparatus as claimed in claim 14, wherein the eccentric pivot point is located closer to the radially outer end of the dog, and wherein the radially outer end of each dog protrudes beyond an circumferential surface of the collar or sleeve, so that the axial movement of the collar or sleeve presses the collar or sleeve against the radially outer end of the dog and disengages the dogs from the chain.

16. An apparatus as claimed in claim 14, wherein the collar or sleeve is resiliently biased out of engagement with the dogs.

17. An apparatus as claimed in claim 14, wherein the collar or sleeve is adapted to be pressed into engagement with the dogs by compression of a resilient device biasing the collar or sleeve away from engagement with the dogs.

18. An apparatus as claimed in claim 14, wherein the collar or sleeve is formed at one axial end of the body, spaced away from the dogs, and is adapted to be moved in and out of engagement with the dogs by a clamp device pressing the sleeve against the body.

19. An apparatus as claimed in claim 1, wherein the chain is comprised in a tension leg structure.

20. An apparatus as claimed in claim 1, wherein the apparatus incorporates an alignment device to control radial alignment of the gripping devices with respect to the chain links.

21. An apparatus as claimed in claim 20, wherein the alignment device comprises a guide device to feed the chain into the body in a defined orientation in which the links of the chain are aligned with the first and second gripping devices.

22. An apparatus as claimed in claim 21, wherein the guide device comprises an inlet mask in the form of an aperture having the same outline as the chain in plan view.

23. An apparatus as claimed in claim 1, further comprising a strain gauge to measure the tension on the chain.

24. A method of gripping a chain, the method comprising providing a body having a body axis and allowing passage of the chain relative to the body along the body axis;

the body having a first chain gripping device, adapted to grip the chain to restrict or prevent movement of the chain relative to the body; and a second chain gripping device, adapted to grip the chain to restrict or prevent movement of the chain relative to the body;

the first and second gripping devices being arranged around the body axis in respective first and second angular orientations towards the body axis which are perpendicular to one another, whereby the first and second chain gripping devices are adapted to grip respective links of the chain that are perpendicular to one another;

wherein the method comprises gripping a first link of the chain with the first gripping device, the first link of the chain being in a first angular orientation and aligned with the first gripping device; and gripping a second link of the chain with the second gripping device, the second link of the chain being in a second angular orientation perpendicular to the first angular orientation and aligned with the second gripping device.

25. A method as claimed in claim 24, the method comprising moving the chain such that when once a single link has moved past the first gripping device in a first direction, it cannot pass back through the first gripping device in the opposite direction to relieve tension on the chain, because the chain is then being held in that position by the second gripping device which engages a different link of the chain.

26. A method as claimed in claim 24, wherein the body is located between an anchor and an object to be anchored, and is suspended from the object so that the chain passes through the gripping devices before connecting to the object being anchored.

27. A method as claimed in claim 26, wherein the body is connected to the object being anchored by a pivotable connection allowing the line of the chain approaching the object to change by swivelling of the pivotable connection whereby torque and lateral forces are isolated from the object by the pivotable connection.

28. A method as claimed in claim 26, adapted to allow tensioning of anchoring chains securing a subsea production buoy to anchoring points on the sea bed.

\* \* \* \* \*